US012565687B2

(12) United States Patent (10) Patent No.: US 12,565,687 B2
Bensouissi et al. (45) Date of Patent: Mar. 3, 2026

(54) GLUCOSE IN SOLID FORM AND PROCESS FOR MANUFACTURING GLUCOSE IN SOLID FORM

(71) Applicant: CARGILL, INCORPORATED, Wayzata, MN (US)

(72) Inventors: Abdelfattah Bensouissi, Vilvoorde (BE); Angelo Chianese, Rome (IT); Marco Stoller, Rome (IT)

(73) Assignee: CARGILL, INCORPORATED, Wayzata, MN (US)

( * ) Notice: Subject to any disclaimer, the term of this patent is extended or adjusted under 35 U.S.C. 154(b) by 798 days.

(21) Appl. No.: 17/760,102

(22) PCT Filed: Feb. 5, 2021

(86) PCT No.: PCT/US2021/016843
§ 371 (c)(1),
(2) Date: Aug. 4, 2022

(87) PCT Pub. No.: WO2021/158932
PCT Pub. Date: Aug. 12, 2021

(65) Prior Publication Data
US 2023/0043868 A1 Feb. 9, 2023

(51) Int. Cl.
| | |
|---|---|
| *C13K 1/10* | (2006.01) |
| *A23K 20/163* | (2016.01) |
| *A23L 29/30* | (2016.01) |
| *A23P 10/40* | (2016.01) |
| *A61K 8/60* | (2006.01) |
| *A61K 47/26* | (2006.01) |
| *C07H 1/00* | (2006.01) |
| *C07H 3/02* | (2006.01) |

(52) U.S. Cl.
CPC .............. *C13K 1/10* (2013.01); *A23K 20/163* (2016.05); *A23L 29/30* (2016.08); *A23P 10/40* (2016.08); *A61K 8/60* (2013.01); *A61K 47/26* (2013.01); *C07H 1/00* (2013.01); *C07H 3/02* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 3,197,338 | A | 7/1965 | Hurst |
| 3,956,009 | A | 5/1976 | Lundquist, Jr. |
| 4,681,639 | A | 7/1987 | Hinck |
| 2003/0005923 | A1 | 1/2003 | Moraly |

FOREIGN PATENT DOCUMENTS

| | | | | |
|---|---|---|---|---|
| EP | 0039123 | B1 | 10/1984 | |
| EP | 0195610 | A2 | 9/1986 | |
| EP | 0140691 | B1 | 8/1988 | |
| EP | 1183264 | B1 | 9/2010 | |
| WO | WO-9428181 | A2 * | 12/1994 | ............... B01D 1/18 |
| WO | WO-2015028784 | A1 * | 3/2015 | ......... A23L 1/22008 |

OTHER PUBLICATIONS

Gordon et al., "Ideal copolymers and the second-order transitions of synthetic rubbers. i. non-crystalline copolymers", Journal of Applied Chemistry, vol. 2, Issue 9, Sep. 1952, pp. 493-500.
Verrijssen et al., "Role of mechanical forces in the stomach phase on he in vitro bioaccessibility of B-carotene", Food Research International 55 (2014) 271-280.
Verrijssen et al., "The effect of pectin concentration and degree of methyl-esterification on the in vitro bioaccessibility of B-carotene-enriched emulsions", Food Research International 57 (2014) 71-78.

* cited by examiner

*Primary Examiner* — Dale R Miller

(57) ABSTRACT
A glucose in solid form containing a matrix phase and a plurality of carbohydrate crystals within said matrix phase, the matrix phase containing amorphous glucose and water, wherein the carbohydrate crystals comprise glucose and optionally one or more other carbohydrate(s), and optionally wherein the glucose in solid form is coated with a dry powder coating. The glucose in solid form may comprise at least 50 wt % dry substance (DS) glucose and may comprise one or more other carbohydrate(s) besides glucose. A method for manufacturing solidified glucose is also provided.

16 Claims, No Drawings

GLUCOSE IN SOLID FORM AND PROCESS FOR MANUFACTURING GLUCOSE IN SOLID FORM

CROSS-REFERENCE TO RELATED APPLICATIONS

This application is a national phase of International Application No. PCT/US2021/016843, filed Feb. 5, 2021, which claims the benefit of European Patent Application No. 20155950.7, filed Feb. 6, 2020, each of which is hereby incorporated by reference herein in its entirety.

FIELD OF THE INVENTION

The present invention relates to solidified glucose, to a process for producing solidified glucose and various uses of the solidified glucose e.g. in food, feed, personal care, nutraceutical, pharmaceutical and industrial applications.

BACKGROUND OF THE INVENTION

Glucose as defined herein is a monosaccharide with the molecular formula $C_6H_{12}O_6$, also known and referred to herein as "dextrose". Glucose has a lower sweetness than sucrose, but the same caloric value as sucrose.

Commercially, glucose, glucose syrups, and glucose-fructose syrups are mainly produced from starch by enzymatic hydrolysis. However, various challenges exist not only in the manufacture but also in the supply chain of glucose.

In the food and pharmaceutical industry, glucose is often provided in the form of syrups e.g. glucose-fructose syrups comprising from 50 to 95% by weight (wt %) dry substance (DS) of glucose or other glucose-containing syrups having at least 50 wt % DS of glucose. Syrups having a low content of glucose and consequently a high content of water, are less preferred by these industries since shipping them would imply higher transportation costs. The syrups typically have short shelf life, which may be due to physical instability (undesirable solidification and microbiological instability due to high water activity), and may be affected by glucose and/or fructose solidification, in particular during storage. Such crystallization is detrimental to the end user in that it changes the glucose content of the product that remains in syrup form and consequently it may become harder to handle. In particular, dosing a syrup which has partially solidified may be increasingly difficult and may render a final end-product containing the syrup, heterogeneous.

Glucose is also available in solid i.e. crystalline form, for example as anhydrous dextrose or dextrose monohydrate (also referred to herein as anhydrous glucose or glucose monohydrate respectively). Crystalline glucose is typically a free-flowing product and consists essentially of glucose crystals with no or only trace amorphous formations. For many applications, glucose in solid, powder form is preferred, and sometimes even required, as it is easier to handle, transport, store and dose than glucose syrups.

A number of prior-art processes describe the production of semi-crystalline monosaccharides. Semi-crystalline means having both crystalline and amorphous phases.

U.S. Pat. No. 4,681,639 relates to a process for producing a flowable dry product made of isoglucose syrup.

U.S. Pat. No. 3,956,009 relates to a process for preparing dried, solid, particulate fructose products from fructose solutions by drying the solution in a current of heated air and in the presence of separately introduced recycled dried product solids.

EP 0 195 610 describes a continuous process for the crystallization of fructose from an aqueous fructose syrup containing at least 90% by weight fructose on a dry solids basis, in which the syrup at a total solids content of at least 95% by weight is rapidly and thoroughly mixed with seed (fructose), at a temperature of 55-75C e.g. for up to 2 minutes; is then deposited on a surface where it is allowed to crystallize under quiescent conditions at a temperature of 50-70° C., until a solid cake is formed; and is then comminuted to provide a free-flowing granular fructose product which can be further dried.

Glucose crystallization processes are, however, difficult to operate, time-consuming, require a separation step such as centrifugation, rather expensive and often result in a low yield of glucose and a large number of by-products, so-called mother liquor or "greens". Normally, in order to obtain solid form glucose (anhydrous dextrose or dextrose monohydrate) a glucose-containing syrup first has to be purified to a level of about 94 wt % dextrose purity by treatment with various enzymes and nanofiltration. Glucose is then crystallised by multiple slow cooling crystallisation steps from the high purity syrup. The resulting mixture is centrifuged in order to separate the mother liquor (also called "greens") from the crystalline glucose material. The mother liquor is a significant waste stream. The long process and low yield is thus costly and disadvantageous, which greatly limits the commercial availability of crystalline glucose for use in food, pharmaceutical and other products.

There is thus a need for glucose in solid form, in particular in powder form, that can be produced in a more cost- and/or time-efficient manner, which does not require high purity glucose-containing syrups as a starting material and which avoids the formation of mother liquor ("greens") waste. In particular, there is a need for a higher-yield process for producing solid glucose, preferably in continuous mode, and in particular a solid glucose powder. There is also a need for cost- and/or time-efficient, high-yield processes, avoiding the formation of mother liquor waste streams, which produce solid glucose of high glucose purity or a solid glucose of specific properties, for example by adding other carbohydrates. There is also a need for such a process to yield a solid glucose powder with long-term stability (its properties do not substantially change with time), easy handling (e.g. good flowability) and good wettability and dissolution speed.

The present invention seeks to mitigate or alleviate the drawbacks of the prior art and to provide an improved solid glucose product and an optimized process for manufacturing thereof.

SUMMARY OF THE INVENTION

The invention relates to a glucose in solid form containing a matrix phase and a plurality of carbohydrate crystals within said matrix phase, the matrix phase containing amorphous glucose and water, wherein the carbohydrate crystals comprise glucose and optionally one or more other carbohydrate(s), and wherein the glucose in solid form is optionally coated with a dry powder coating. Preferably, the glass transition temperature (Tg) of the dry powder coating is higher than the ambient temperature. Preferably, the amount of glucose in the solid form is at least 50 wt % on a dry substance (DS) basis. Preferably, the glucose in the solid form comprises one or more other carbohydrate(s) besides glucose.

The matrix phase containing amorphous glucose preferably has a Tg higher than the ambient temperature. However, if the overall Tg of the matrix phase has a Tg lower than the ambient temperature, then the glucose in solid form is preferably coated with a dry powder coating that has a Tg higher than the ambient temperature.

If the matrix phase and the carbohydrate crystals essentially consist of or consist only of glucose and water, then the glucose in solid form is preferably coated with a dry powder coating, wherein the dry powder coating is preferably different from or does not essentially consist or consist only of glucose. Preferably, the Tg of the dry powder coating is higher than the ambient temperature.

The invention also relates to a glucose in solid form containing a matrix phase and a plurality of glucose crystals within said matrix phase, the matrix phase containing amorphous glucose and water, wherein the glucose in solid form is preferably coated with a dry powder coating, preferably with a dry powder coating that is different from or does not essentially consist or consist only of glucose. Preferably, the Tg of the dry powder coating is higher than the ambient temperature.

The invention also relates to a powder containing particles, the particles comprising the glucose in solid form.

The inventors observed that the glucose in solid form in accordance with the invention, hereinafter "the inventive glucose", can be produced in a time- and cost-efficient manner In addition, the inventive glucose is of a high purity, good flowability, wettability, dispersibility and dissolution speed, and long-term stability. By adding other carbohydrates it is also possible to obtain other specific properties of the inventive glucose, also with good flowability, wettability, dispersibility and dissolution speed and long-term stability.

The invention, further relates to a method of manufacturing solidified glucose, in particular the inventive glucose, comprising:

(i) Providing an aqueous glucose solution having a dry substance (DS) of at least 80 wt % relative to the total mass of the solution and preferably at least 50 wt % DS of glucose and optionally one or more other carbohydrate(s) besides glucose;

(ii) Providing a powder containing particles comprising a carbohydrate material;

(iii) Adding the powder to the aqueous glucose solution to obtain an aqueous slurry having a glass transition temperature (Tg) higher than the ambient temperature;

(iv) Cooling the aqueous slurry to a temperature of at most the Tg of said slurry thereby obtaining a product containing solidified glucose;

(v) Optionally milling the product containing the solidified glucose and/or coating the solidified glucose or the milled solidified glucose.

The inventors observed that the process in accordance with the invention, hereinafter "the inventive process", can produce the inventive glucose in a cost- and time-efficient manner but also in high yield. In particular, the inventive process may be designed to run with increased efficiency in the sense that a low amount of energy and/or the amount of waste material (e.g. mother liquor) may be kept to a minimum and even to zero waste. This means a syrup having a low glucose purity as the starting material can be used. Consequently, there may be no need of a recycling step of liquid waste streams in the inventive process. Furthermore, the obtained solid glucose powder is stable and can be handled easily. Other advantages of the invention will become apparent from the detailed description given hereunder.

The invention further relates to a food, feed, personal care, nutraceutical pharmaceutical or industrial product comprising the inventive glucose. The food, feed, personal care, nutraceutical, pharmaceutical or industrial product may comprise additional ingredients.

The invention further relates to the inventive glucose or the inventive powder obtainable according to the inventive process.

DETAILED DESCRIPTION OF THE INVENTION

The invention relates to a glucose in solid form containing a matrix phase and a dispersed phase, the dispersed phase being dispersed within said matrix phase, the matrix phase containing amorphous glucose and the dispersed phase containing a plurality of carbohydrate crystals, wherein optionally the glucose in solid form is coated with a dry powder coating.

Preferably, the "one or more other carbohydrate(s) besides glucose" are selected from sweeteners and/or polyols. Preferably the sweetener is selected from fructose, maltose, isomaltulose, mannose, sucrose, lactose, trehalose, galactose, allulose, tagatose, sucromalt, raffinose and mixtures thereof. Preferably the polyol is selected from erythritol, threitol, arabinitol, ribitol, allitol, altritol, gulitol, galactitol, talitol, lactitol, sorbitol, xylitol, erythritol, maltitol, isomalt, isomaltitol, mannitol and mixtures thereof. More preferably the sweetener is selected form fructose, sucrose, maltose, isomaltulose, lactose, raffinose and mixtures thereof. More preferably the polyol is selected from maltitol, isomalt, mannitol and mixtures thereof.

Preferably, the glucose in solid form contains at least 50 wt % DS of glucose, more preferably at least 60 wt % DS of glucose and most preferably at least 70 wt % DS of glucose. Preferably, the glucose in solid form contains at most 99 wt % DS of glucose, more preferably at most 95 wt % DS of glucose, even more preferably at most 90 wt % DS of glucose and most preferably at most 80 wt % of glucose. Preferably, the glucose in the solid form comprises one or more other carbohydrate(s) besides glucose. For instance, the glucose in solid form may comprise or (essentially) consist of less than 50 wt % DS of one or more other carbohydrate(s) besides glucose and at least 50 wt % DS of glucose; for instance, 40 wt % DS of one or more other carbohydrate(s) besides glucose and 60 wt % DS glucose; or for instance, 42 wt % DS of one or more other carbohydrate(s) besides glucose and 53 wt % DS glucose. For instance, the glucose in solid form may comprise or (essentially) consist of less than 50 wt % DS fructose and at least 50 wt % DS of glucose; for instance, 40 wt % DS fructose and 60 wt % DS glucose; or for instance, 42 wt % DS fructose and 53 wt % DS glucose.

The carbohydrate crystals can be crystals comprising glucose and optionally one or more other carbohydrate(s).

Preferably the matrix phase comprising amorphous glucose has an overall glass transition temperature (Tg) higher than the ambient temperature.

By "ambient temperature" it is meant herein room temperature. Generally, room temperature is a temperature in the range of 20° C. to 25° C.

The overall Tg of the matrix phase can be estimated using the Gordon-Taylor equation (M. Gordon, J. S. Taylor, *J. Appl. Chem.* 2, 495 (1952)).

If the matrix phase has a Tg lower than the ambient temperature, then the glucose in solid form is preferably coated with a dry powder coating that has a Tg higher than the ambient temperature.

By "a Tg higher than the ambient temperature", it is meant in this description preferably at least 1° C., at least 2° C., at least 3° C., at least 4° C., at least 5° C., at least 6° C., at least 7° C., at least 8° C., at least 9° C. or at least 10° C. higher than the ambient temperature.

By "a Tg lower than the ambient temperature", it is meant in this description preferably at least 1° C., at least 2° C., at least 3° C., at least 4° C., at least 5° C., at least 6° C., at least 7° C., at least 8° C., at least 9° C. or at least 10° C. lower than the ambient temperature.

However, if the matrix phase and the carbohydrate crystals essentially consist of or consist only of glucose and water, then the glucose in solid form is preferably coated with a dry powder coating, wherein the dry powder coating preferably is different from or does not essentially consist or consist only of glucose.

The invention also relates to a glucose in solid form, containing a matrix phase and a dispersed phase, the dispersed phase being dispersed within said matrix phase, the matrix phase containing amorphous glucose and the dispersed phase containing a plurality of glucose crystals. In such a case, where the matrix phase and the dispersed phase essentially consist or consist only of glucose and water, the glucose in solid form is preferably coated with a dry powder coating, preferably with a dry powder coating that is different from or does not essentially consist or consist only of glucose. The dry powder coating preferably has an overall glass transition temperature (Tg) higher than the ambient temperature. By "a Tg higher than the ambient temperature", it is meant preferably at least 1° C., at least 2° C., at least 3° C., at least 4° C., at least 5° C., at least 6° C., at least 7° C., at least 8° C., at least 9° C. or at least 10° C. higher than the ambient temperature.

The invention also relates to a powder containing particles comprising the inventive glucose.

The following applies to all of the inventive glucose, inventive powder and inventive processes for making the inventive glucose and inventive powder disclosed herein:

The inventive glucose is in solid form, i.e. said glucose can essentially retain its shape for at least 1 hour when placed on a flat surface at a temperature less than 40° C. and at a relative humidity less than 80%. The inventive glucose may have any regular or irregular shape, e.g. powder, fibres, a block, and the like.

The inventive glucose contains a matrix phase and a dispersed phase. The matrix phase is herein understood a continuous phase embedding the dispersed phase. The dispersed phase is dispersed, preferably homogeneously, inside the matrix phase.

Preferably, the matrix phase in the inventive glucose is present in an amount of at least 70 wt %, preferably at least 80 wt %, more preferably at least 90 wt %, even more preferably at least 95 wt %.

The matrix phase of the inventive glucose contains amorphous glucose. By amorphous glucose is herein understood a solid formed at non-equilibrium conditions either by removing the dispersing medium (such as water), or from the melt by cooling, or by rapid supercooling. The amorphous glucose is preferably present in an amount of at least 0.1 wt % relative to the total mass of the inventive glucose, more preferably at least 5 wt %, most preferably at least 10 wt %. Preferably, said amount of amorphous glucose is at most 80 wt %, more preferably at most 30 wt %, most preferably at most 25 wt %. Preferably, said amount of amorphous glucose is between 0.1 wt % and 80 wt %, more preferably between 5 wt % and 25 wt %, most preferably between 10 wt % and 15 wt %.

The matrix phase may also contain water. The water is preferably present within the matrix phase in an amount of preferably at least 0.2 wt % relative to the total mass of the inventive glucose, more preferably at least 2 wt %, most preferably at least 5 wt %. Preferably, said amount of water is at most 10 wt %, more preferably at most 8 wt %, most preferably at most 7 wt %. Preferably, said amount of water is between 0.2 wt % and 10 wt %, more preferably between 2 wt % and 8 wt %, most preferably between 5 wt % and 7 wt %.

The matrix phase may also contain impurities typically in an amount of between 1 and 20 wt %. These may be impurities initially present in the glucose solution or introduced during the manufacturing process.

The dispersed phase is distributed inside the matrix phase, said dispersed phase containing carbohydrate crystals comprising glucose crystals and optionally one or more other carbohydrate(s). By being distributed inside the matrix phase it is herein understood that the crystals are distributed or dispersed inside said matrix phase. Said crystals may be present inside the matrix phase as singular crystals or as clusters as crystals or combinations thereof. By crystals is herein understood as including the solid material (preferably carbohydrate material) added to the solution to give rise to the aqueous slurry of step iii. This slurry may enhance the crystallization of the solute glucose in the matrix phase. The dispersed phase is preferably present in an amount of at least 3 wt % relative to the total mass of the inventive glucose, more preferably at least 5 wt %, 10 wt %, 15 wt % or 20 wt %, even more preferably at least 70 wt %, most preferably at least 75 wt %. Preferably, said amount of carbohydrate crystals, including glucose crystals, is at most 99.8 wt %, more preferably at most 90 wt %, most preferably at most 80 wt %. Preferably, said amount of carbohydrate crystals, including glucose crystals, is between 3 wt % and 99.8 wt %, more preferably between 5 wt %, 10 wt %, 15 wt % or 20 wt % and 99.8 wt %, even more preferably between 70 wt % and 90 wt %, most preferably between 75 wt % and 80 wt %. The amount of crystals will depend on the particle size of the crystals introduced and on the occurrence of spontaneous nucleation during the solidification.

The one or more other carbohydrates can be present from at least 1, at least 3, at least 5, at least 10, at least 15, at least 20, at least 30, at least 40, at least 50, at least 60, at least 70, at least 80, at least 90, at least 92, at least 95, at least 97, at least 98, at least 99 or at least 99.5 wt % of the total amount of carbohydrate crystals present in the inventive glucose. The one or more other carbohydrates can be present up to at most 99.5, at most 99, at most 98, at most 97, at most 95, at most 92, at most 90, at most 80, at most 70, at most 60, at most 50, at most 40, at most 30, at most 20, at most 15, at most 10, at most 5, at most 3 or at most 1 wt % of the of the total amount of carbohydrate crystals present in the inventive glucose.

The carbohydrate crystals can be crystals comprising glucose and optionally one or more other carbohydrate(s). Preferably, the one or more carbohydrate(s) are selected from sweeteners and/or polyols. Preferably the sweetener is selected from fructose, maltose, isomaltuose, mannose, sucrose, lactose, trehalose, allulose, galactose, raffinose, trehalose, tagatose, isomaltulose, sucromalt and mixtures thereof. Preferably the polyol is selected from erythritol, threitol, arabinitol, ribitol, allitol, altritol, gulitol, galactitol, talitol, lactitol, sorbitol, xylitol, erythritol, maltitol, isomalt, isomaltitol, mannitol and mixtures thereof. Most preferably the sweetener is selected form fructose, sucrose, maltose, isomaltulose, lactose, raffinose and mixtures thereof. Most preferably the polyol is selected from sorbitol, maltitol, isomalt, mannitol and mixtures thereof. The carbohydrate crystals, which have been added during the seeding process (i.e. in step iii), can therefore be different from or do not (essentially) consist of crystals of glucose.

If the matrix phase and the dispersed phase essentially consist or consist only of glucose and water, then the glucose in solid form is preferably coated with a dry powder coating, wherein the dry powder coating preferably is different from glucose or does not essentially consist or consist only of glucose. The dry powder coating preferably has an overall glass transition temperature (Tg) higher than the ambient temperature. By "a Tg higher than the ambient temperature", it is meant preferably at least 1° C., at least 2° C., at least 3° C., at least 4° C., at least 5° C., at least 6° C., at least 7° C., at least 8° C., at least 9° C. or at least 10° C. higher than the ambient temperature.

Suitable coating material is described below and will not be repeated here.

The matrix phase and/or the dispersed phase may further contain internally, various carbohydrates, such as sweeteners, polyols and the like. The sweetener may be a nutritive sweetener, a high intensity sweetener, other sweeteners and mixtures thereof. Non-limiting examples of nutritive sweeteners include sucrose, maltose, lactose, fructose, allulose and galactose. Non-limiting examples of other sweeteners also include trehalose, tagatose, isomaltulose and sucromalt. Non-limiting examples of high intensity sweetener also include aspartame, advantame, acesulfame salts such as acesulfame-K, alitame, saccharin, cyclamate, sucralose, alitame, neotame, stevia, steviol glycosides, stevia leaf extracts, glycyrrhizin, neohesperidin dihydrochalcone, monellin, thaumatin, brazzein, mogrosides (and other sweeteners found in monk fruit), and mixture of two or more thereof. Preferably the high intensity sweetener is stevia, a stevia leaf extract or steviol glycoside(s). The polyol may be selected among the tetritols, pentitols, hexitols, hydrogenated disaccharides, hydrogenated trisaccharides, hydrogenated tetrasaccharides, hydrogenated maltodextrins and mixture thereof.

More specifically, the polyol can be selected from the group consisting of erythritol, threitol, arabinitol, xylitol, ribitol, allitol, altritol, gulitol, galactitol, mannitol, sorbitol, talitol, maltitol, isomaltitol, isomalt, lactitol and mixtures of two or more thereof. Preferably the polyol is maltitol, mannitol, isomalt or a mixture of two or more thereof.

Preferably the matrix phase comprising amorphous glucose has an overall glass transition temperature (Tg) higher than the ambient temperature. By "a Tg higher than the ambient temperature", it is meant preferably at least 1° C., at least 2° C., at least 3° C., at least 4° C., at least 5° C., at least 6° C., at least 7° C., at least 8° C., at least 9° C. or at least 10° C. higher than the ambient temperature.

The overall Tg of the matrix phase can be estimated using the Gordon-Taylor equation (M. Gordon, J. S. Taylor, *J. Appl. Chem.* 2, 495 (1952)).

If the matrix phase has a Tg lower than the ambient temperature, then the glucose in solid form is preferably coated with a dry powder coating that has a Tg higher than the ambient temperature. By "a Tg lower than the ambient temperature", it is meant preferably at least 1° C., at least 2° C., at least 3° C., at least 4° C., at least 5° C., at least 6° C., at least 7° C., at least 8° C., at least 9° C. or at least 10° C. lower than the ambient temperature.

By "containing internally" it is herein understood that the carbohydrates are present inside said phases, i.e. in the bulk. If present, the carbohydrate material is preferably comprised in an amount of at most 49 wt % DS, relative to the total combined amount of the matrix and dispersed phases, preferably at most 25 wt % DS, more preferably at most 20 wt % DS, even more preferably at most 15 wt % DS, yet even more preferably at most 10 wt % DS, yet even more preferably at most 5 wt % DS, yet even more preferably at most 2 wt % DS, most preferably at most 1 wt % DS.

The inventive glucose is preferably in the form of a powder. The powder contains particles comprising the inventive glucose and preferably having a D50 of at least 10 μm, more preferably at least 50 μm, even more preferably at least 100 μm, most preferably at least 150 μm. Preferably, said D50 is at 2500 μm, more preferably at most 700 μm, even more preferably at most 300 μm, most preferably at most 200 μm. Preferably, said D50 is between 10 μm and 2500 μm, more preferably between 50 μm and 700 μm, most preferably between 150 μm and 200 μm.

Preferably, the particles have a D90 of preferably at least 20 μm, more preferably at least 80 μm, even more preferably at least 150 μm, most preferably at least 200 μm. Preferably, said D90 is at most 2000 μm, more preferably at most 1000 μm, even more preferably at most 500 μm. Preferably, said D90 is between 20 μm and 2000 μm, more preferably between 80 μm and 1000 μm, most preferably between 100 μm and 500 μm.

The particle size distributions D50 and D90 and the mean particle diameters (mean volume diameter of particle diameters: MV) of the particles forming the powder were measured by laser diffraction (Beckman Coulter, LS 13 320, Miami, Florida) as detailed in the MEASURING METHODS section of the description.

Preferably, said particles are coated with a dry powder coating, which may advantageously provide said particles with non-stickiness abilities and may provide the powder with good flow properties. By dry powder coating is herein understood a coating in the form of a powder having a moisture content of at most 10 wt % based on the total weight of the powder. Preferably, the moisture content is at least 0.1 wt %, more preferably at least 1 wt %, even more preferably at least 2 wt %, most preferably at least 5 wt %. Preferably, said moisture content is at most 10 wt %, more preferably at most 8 wt %, most preferably at most 7 wt %. Preferably, said moisture content is between 0.1 wt % and 10 wt %, most preferably between 0.1 wt % and 8 wt %.

The dry powder coating contains coating particles, said coating particles having a D50 that is at least 15% smaller than the D50 of the particles forming the powder, more preferably at least 20% smaller, even more preferably at least 25% smaller, yet even more preferably at least 30% smaller, most preferably at least 35% smaller. Preferably, said coating particles are at most 75% smaller than the D50 of the particles forming the powder, more preferably at most 60% smaller, most preferably at most 60% smaller.

Any material may be used for the particles of the dry powder coating. This is preferably any material that can prevent any water absorption and/or stickiness of the inventive glucose. The dry powder coating is thus preferably non-hygroscopic. Preferably, the coating particles contain a carbohydrate material. Preferably, the Tg of the dry powder coating is higher than the ambient temperature. More preferably, the Tg of the dry powder coating is at least 1° C., at least 2° C., at least 3° C., at least 4° C., at least 5° C., at least 6° C., at least 7° C., at least 8° C., at least 9° C. or at least 10° C. higher than the ambient temperature. Non-limiting examples of the carbohydrate material include sweeteners, starches including modified starches, hydrocolloids, polyols, dextrins, maltodextrins, food-grade polymers, biopolymers and the like and mixtures thereof. Most preferred carbohydrate materials are sweeteners and polyols.

The sweetener may be a nutritive sweetener, a high intensity sweetener and mixtures thereof. Non-limiting examples of nutritive sweeteners include sucrose, maltose, lactose, fructose, allulose and galactose. The nutritive sweetener may also be a glucose different than the inventive glucose, preferably a crystalline glucose with a crystallinity of above 95%. Other sweeteners also include trehalose, tagatose, isomaltulose and sucromalt. The high intensity sweetener may be selected among aspartame, advantame, acesulfame salts such as acesulfame-K, alitame, saccharin, cyclamate, sucralose, alitame, neotame, stevia, steviol glycosides, stevia leaf extracts, glycyrrhizin, neohesperidin dihydrochalcone, monellin, thaumatin, brazzein, mogrosides (and other sweeteners found in monk fruit), and mixture of two or more thereof. Preferably the high intensity sweetener is stevia, a stevia leaf extract or steviol glycoside(s).

The polyol may be selected among the tetritols, pentitols, hexitols, hydrogenated disaccharides, hydrogenated trisaccharides, hydrogenated tetrasaccharides, hydrogenated maltodextrins and mixture thereof. More specifically, the polyol can be selected from the group consisting of erythritol, threitol, arabinitol, xylitol, ribitol, allitol, altritol, gulitol, galactitol, mannitol, sorbitol, talitol, maltitol, isomaltitol, isomalt, lactitol and mixtures of two or more thereof. Preferably the polyol is maltitol, mannitolisomalt or a mixture of two or more thereof.

In case a material with a low glass transition temperature (below the ambient temperature) is used as a dry coating powder, e.g. polyols such as sorbitol, erythritol, xylitol, they should can be combined with other materials to raise the average glass transition temperature to above the ambient temperature.

In a preferred embodiment, the dry powder coating contains particles containing the inventive glucose and having a particle size distribution within the ranges described hereinabove in relation to said coating. The dry powder coating of this embodiment can be obtained by finely milling the inventive glucose.

Preferably, the dry powder coating contains particles comprising stevia, a stevia leaf extract, steviol glycoside(s), mannitol, glucose different than the inventive glucose, the inventive glucose or mixtures thereof.

However, if the matrix phase and the carbohydrate crystals essentially consist or consist only of glucose and water, then the dry powder coating preferably is different from or does not essentially consist or consist only of glucose, but may contain one or more of the carbohydrate materials mentioned for the dry coating above.

The invention further relates to a powder (hereinafter referred to as "the inventive powder") containing particles, said particles comprising the inventive glucose. Preferred embodiments of the particles are given hereinabove and will not be repeated herein.

Preferably the inventive powder has a moisture content of from 0.1 to 10 wt %.

The inventors observed that the inventive glucose and the inventive powder may have high dissolution speeds. The solubility (maximum amount that can be dissolved at a given temperature at equilibrium) can be further optimized by combining specific carbohydrates with the glucose in the matrix phase.

The particles forming the inventive powder may also be in the form of agglomerates. If present, said agglomerates preferably have a mean diameter of from 0.2 to 10 mm, more preferably from 0.3 to 5 mm, most preferably from 0.8 to 1.5 mm Mean diameter may be measured by means of a sieving procedure and/or dimensional analysis of images under an optical microscope.

The inventors surprisingly observed that the inventive glucose has a white colour, i.e. it is characterized by a CIELAB L* value of at least 85, more preferably at least 90, most preferably at least 95. Preferably, the CIELAB b* value is at most 100, more preferably at most 99, most preferably at most 98.

The inventors surprisingly observed that the inventive powder has an optimum flowability. Preferably, the flowability of said powder is between 20 and 45 degrees [Angle of response], more preferably between 25 and 45, most preferably between 30 and 35.

The inventors surprisingly observed that the inventive powder and/or the inventive glucose may have an optimum hydrophilicity. Preferably, the hydrophilicity thereof is between 15% and 50% [mass increase at standard test conditions mentioned below], more preferably between 20% and 45%, most preferably between 30% and 40%.

The invention, further relates to a method of manufacturing solidified glucose, in particular the inventive glucose, (hereinafter the "inventive method") comprising:

(i) Providing an aqueous glucose solution having a dry substance (DS) of at least 80 wt % relative to the total mass of the solution and preferably at least 50 wt % DS of glucose and optionally one or more other carbohydrate(s) besides glucose;

(ii) Providing a powder containing particles comprising a carbohydrate material;

(iii) Adding the powder to the aqueous glucose solution to obtain an aqueous slurry having a glass transition temperature (Tg) higher than the ambient temperature, preferably at least 1° C. higher than the ambient temperature;

(iv) Cooling the aqueous slurry to a temperature of at most the Tg of said slurry thereby obtaining a product containing solidified glucose;

(v) Optionally milling the product containing the solidified glucose and/or coating the solidified glucose or the milled solidified glucose.

Preferably, the "optionally one or more other carbohydrate(s)" besides glucose are selected from sweeteners and/or polyols. Preferably the sweetener is selected from fructose, maltose, isomaltulose, mannose, sucrose, lactose, trehalose, galactose, allulose, tagatose, sucromalt, raffinose and mixtures thereof. Preferably the polyol is selected from erythritol, threitol, arabinitol, ribitol, allitol, altritol, gulitol, galactitol, talitol, lactitol, sorbitol, xylitol, erythritol, maltitol, isomalt, isomaltitol, mannitol and mixtures thereof. More preferably the sweetener is selected form fructose, sucrose, maltose, isomaltulose, lactose, raffinose and mixtures thereof. More preferably the polyol is selected from maltitol, isomalt, mannitol and mixtures thereof.

Preferably, the aqueous glucose solution provided in step (i) has at least 50 wt % DS of glucose, more preferably at least 60 wt % DS of glucose and most preferably at least 70 wt % DS of glucose. Preferably, the aqueous glucose solution provided in step (i) has at most 99 wt % DS of glucose, more preferably at most 95 wt % DS of glucose, even more preferably at most 90 wt % DS of glucose and most preferably at most 80 wt % of glucose. For instance, the aqueous glucose solution may comprise or (essentially) consist of less than 50 wt % DS of one or more other carbohydrate(s) besides glucose and at least 50 wt % DS of glucose; for instance, 40 wt % DS of one or more other carbohydrate(s) besides glucose and 60 wt % DS glucose; or for instance, 42 wt % DS of one or more other carbohydrate(s) besides glucose and 53 wt % DS glucose. For instance, the aqueous glucose solution may comprise or (essentially) consist of less than 50 wt % dry DS fructose and at least 50 wt % DS of glucose; for instance, 40 wt % DS fructose and 60 wt % DS glucose; or for instance, 42 wt % DS fructose and 53 wt % DS glucose.

By "a Tg higher than the ambient temperature", it is meant preferably at least 1° C., at least 2° C., at least 3° C., at least 4° C., at least 5° C., at least 6° C., at least 7° C., at least 8° C., at least 9° C. or at least 10° C. higher than the ambient temperature.

The aqueous glucose solution of step (i) preferably has a DS of at least 85 wt %, more preferably at least 90 wt %. Preferably said DS is from 90 to 99.9 wt %, more preferably from 94 to 98 wt %, most preferably from 96 to 98 wt %.

Preferably, the temperature of the aqueous glucose solution is set from 50° C. to 90° C., more preferably from 50 to 70° C., even more preferably from 55 to 65° C. Preferably, the aqueous glucose solution is maintained at such temperature under constant or regular stirring. Preferably, the aqueous glucose solution is kept under conditions such that the DS does not change. Any suitable means to maintain the aqueous glucose at a said temperature may be used and any suitable means of stirring may be used.

The aqueous glucose solution may be obtained for example by concentration of a less concentrated aqueous glucose solution such as an aqueous glucose solution having a DS content being less than the DS content of the aqueous glucose solution of step (i). For example, said less concentrated aqueous glucose solution may have a DS content of from 10 wt % to less than 80 wt %, or from 20 wt % to 70 wt %, or from 30 wt % to 50 wt %, or from 35 wt % to 45 wt %. Said less concentrated aqueous glucose solution preferably has a glucose purity of from 50 to 99 wt %, preferably from 60 to 95 wt %, more preferably from 70 to 95 wt %, even more preferably from 80 to 95 wt %, yet even more preferably from 90 to 95 wt %. By glucose purity it is herein understood glucose mass per overall DS mass.

Concentration of the less concentrated aqueous glucose solution may be done by evaporation. Evaporation may be done by heating said less concentrated glucose solution at a temperature suitable to remove water without affecting significantly the physicochemical properties, such as color, of the glucose in the solution, e.g. under vacuum. The evaporation temperature may be for example from 50 to 90° C., preferably from 50 to 70° C., more preferably from 55 to 65° C. Heating may be carried out in a double jacketed vessel using water or any higher boiling point fluid as heating medium. Preferably heating is done in a closed system from which water is removed in a controlled manner in order to obtain the desired DS. Preferably, stirring is applied during heating. More preferably continuous stirring is applied.

In step (ii) of the inventive method, a powder containing particles comprising a carbohydrate material is provided. The particles preferably have a diameter (considering said particles spheres) of preferably at most 3 mm, more preferably at most 2 mm Preferably said diameter is at least 150

µm, more preferably at least 500 µm. Most preferably the particles have a particle size diameter of from 30 to 500 µm.

The carbohydrate material may comprise or (essentially) consist of one or more carbohydrate(s). The powder may thus contain particles, which comprise or (essentially) consist of one or more carbohydrate(s).

The carbohydrate material may comprise or (essentially) consist of glucose and optionally one or more carbohydrate(s). The powder may thus contain particles, which comprise or (essentially) consist of glucose and optionally one or more carbohydrate(s).

The carbohydrate material may comprise or (essentially) consist of one or more carbohydrate(s) excluding glucose. The powder may thus contain particles, which comprise or (essentially) consist of one or more carbohydrate(s) excluding glucose.

Preferably, the one or more carbohydrate(s) are selected from sweeteners and/or polyols. Preferably the sweetener is selected from fructose, maltose, isomaltulose, mannose, sucrose, lactose, trehalose, galactose, allulose, tagatose, sucromalt, raffinose and mixtures thereof. Preferably the polyol is selected from erythritol, threitol, arabinitol, ribitol, allitol, altritol, gulitol, galactitol, talitol, lactitol, sorbitol, xylitol, erythritol, maltitol, isomalt, isomaltitol, mannitol and mixtures thereof. More preferably the sweetener is selected form fructose, sucrose, maltose, isomaltulose, lactose, raffinose and mixtures thereof. More preferably the polyol is selected from maltitol, isomalt, mannitol and mixtures thereof.

Further suitable examples of the carbohydrate material are given hereinabove in reference to the dry powder coating and will not be repeated herein. Preferably, said material is one or more nutritive sweeteners, one or more polyols (e.g. isomalt or mannitol), one or more high intensity sweeteners (e.g. stevia) or mixtures thereof. Most preferably, said carbohydrate material is the inventive glucose and/or the inventive powder, most preferably the inventive powder. When the inventive glucose and/or the inventive powder is/are used, the process may use any of the other carbohydrate materials to produce said powder and/or said glucose in a suitable quantity for being used in step (ii) of the inventive method.

At step (iii) of the inventive method, the powder is added to the aqueous glucose solution to obtain an aqueous slurry. Preferably, the addition is done by mixing. Mixing is preferably carried out to achieve a homogeneous slurry, i.e. a slurry wherein the powder is homogeneously distributed. Mixtures and in particular homogeneous mixtures can be achieved by mixing the said powder and said solution at preferably constant temperature. Preferably, step (iii) is carried out at a temperature of at least 60° C., more preferably at least 65° C., even more preferably at least 68° C., most preferably at least 70° C. Preferably, said solution temperature is at most 90° C., more preferably at most 85° C., even more preferably at most 80° C., most preferably at most 75° C. Preferably, step (iii) is carried out by mixing at a temperature as indicated hereinabove. Mixing can be carried out with any mixing device known in the art such as for example a static mixing device, a high-speed mixing device and the like.

Mixing can be carried out for a mixing time of at least 1 sec and up to 3 hours. Preferably the mixing time is from 30 s to 40 minutes, more preferably from 1 minute to 30 minutes, even more preferably from 5 minutes to 20 minutes, most preferably from 15 minutes to 25 minutes.

During the mixing, the aqueous glucose solution and the powder are forming a slurry. The difference between a solution and a slurry is well known in the art, i.e. a slurry is a mixture containing the powder in solid phase dispersed within a liquid phase and may also contain dissolved powder. A solution on the other hand means that the powder is dissolved and essentially no solid-phase exists therein.

Optionally, the Tg of the aqueous slurry can be increased when necessary to reach a Tg higher than the ambient temperature by instantaneously evaporating part of the water. This can be done for instance on a heated rotating support. Such rotating disc will ensure concentration of the slurry whilst dividing the slurry into fine droplets containing solid particles.

Step (iii) of the inventive method may also be referred to as 'seeding'. Seeding may induce glucose crystallization to some extent. Preferably the powder is mixed with the aqueous glucose solution in an amount of from 1 to 30 wt %, more preferably from 1 to 20 wt %, more preferably from 1 to 15 wt %, even more preferably from 1 to 10 wt %, yet even more preferably from 2 to 10 wt %, yet even more preferably from 3 to 10 wt %, yet even more preferably from 4 to 10 wt %, yet even more preferably from 5 to 10 wt %, most preferably from 8 to 10 wt %, based on the weight of the glucose solution provided in step (i).

The aqueous slurry is characterized by a glass transition temperature (Tg). The Tg is the temperature at which a reversible transition occurs between a solid amorphous (glassy) state and a supercooled liquid (rubbery) state and is a parameter of critical importance to the stability of amorphous materials. Tg can be measured by using differential scanning calorimetry (DSC). Typically, to determine Tg a sample of the material is first cooled with 10° C./min and then heated with that same speed. For example, amorphous glucose is typically characterized by a glass transition temperature of 31° C. at 100 wt % DS (i.e. completely dry). However, it is well known that a change in the composition of the amorphous glucose (increase in moisture content, presence of other components (for instance other carbohydrates including monosaccharides such as fructose) can significantly affect the Tg. In particular, depending on the composition of the glucose slurry and the type of carbohydrate material used in the seeding step, the glass transition temperature can be varied. Preferably, the Tg of the aqueous slurry of step (iii) of the inventive method is higher than the ambient temperature. By "a Tg higher than the ambient temperature", it is meant preferably at least 1° C., at least 2° C., at least 3° C., at least 4° C., at least 5° C., at least 6° C., at least 7° C., at least 8° C., at least 9° C. or at least 10° C. higher than the ambient temperature.

In step (iv), the slurry is cooled to a temperature of at most the Tg of said slurry, i.e. a temperature equal to or below said Tg. The aim of this step is to cause the formation of a product (a slurry containing solidified glucose) in a glassy state. Cooling to said temperature induces therefore the formation of solidified glucose inside the aqueous slurry and produces therefore a product containing said solidified glucose. The product may also contain (small amounts of) water and the carbohydrate material.

Preferably, the aqueous slurry is cooled at a cooling temperature of 1° C. below the Tg of said slurry, more preferably of at least 3° C., even more preferably of at least 5° C., most preferably of at least 10° C. below the Tg of said slurry.

Cooling is preferably performed under atmospheric conditions at controlled humidity in order to prevent condensation of ambient moisture. Preferably cooling is done in the presence of nitrogen or other inert gas. Preferably, the cooling is carried out in a cooling environment having a relative humidity of from 0 to 70%, more preferably from 0 to 10%, most preferably from 0 to 5%. Preferably, the cooling is rapid or quick cooling, i.e. quenching. The cooling is preferably carried out with a cooling of between 40 and 120° C./sec, more preferably of between 50 and 100° C./sec, most preferably of between 60 and 80° C./sec.

Cooling may be performed by feeding the aqueous slurry into or onto cooling means. Preferably, said cooling means is provided with means to keep the cooling temperature constant and continuously remove the solidification heat released during the solidification process. In case the slurry contains substantial amount of water such that the dextrose cannot be dissolved at reasonable temperatures to avoid color formation, the cooling means can also include a means to instantaneously evaporate water in order to increase the Tg of the slurry higher than the ambient temperature.

The cooling means may be a refrigerated surface, such as a refrigerated belt or refrigerated (revolving) disk for example. The cooling means may also be a cooled gas stream e.g. a cooled air stream or a cooled stream of nitrogen.

Advantageously, the feeding of the aqueous slurry into or onto the cooling means, is done in such a way that the obtained solidified glucose is in the form of particles, threads or filaments. The particles, threads or filaments may be of various sizes, e.g. various diameters, lengths and widths.

Preferably the feeding is carried out such that particles or agglomerated particles are formed, said particles being preferably essentially spherical. If agglomerates are formed, the mean diameter of the agglomerates is preferably from 0.2 to 10 mm, more preferably from 0.3 to 5 mm, most preferably from 0.8 to 1.5 mm. To achieve such particles and/or agglomerates, the aqueous slurry may be fed to the cooling means in the form of droplets containing solid particles. Most preferably, cooling is done by feeding the aqueous slurry in the form of droplets containing solid particles onto a refrigerated belt.

After cooling, the product obtained may be milled in order to reduce its particle size to a desired particle size. Preferably, after milling, the product is obtained in the form of granules or agglomerates having a mean diameter of from 0.3 to 4 mm, more preferably from 0.8 to 1.5 mm Milling is thus not required in case the mean diameter of the agglomerates obtained after cooling is already in said range.

Milling can be done using standard milling apparatus such as fine cutting mills, externally refrigerated to operate below the glass transition temperature of the solidified product. Preferably also milling is performed under atmospheric conditions at controlled humidity. The relative humidity may be from 0 to 70%, preferably from 0 to 10%, more preferably from 0 to 5%. In case of stickiness, the product can be cryogenically milled.

After cooling, or after milling in case a milling step is performed, the solidified glucose may be coated with the dry powder coating described above in the present description. The temperature during the coating step does not need to be strictly controlled. It is increased at or above the glass transition temperature range, preferably coating temperature should stay just higher than the ambient temperature i.e. preferably not more than 20° C., more preferably not more than 15° C., most preferably not more than 10° C. above the ambient temperature. This can easily be finetuned according to common general knowledge of the skilled person. After coating, the solidified glucose may be stored at ambient temperature or it may be refrigerated. Preferably it is stored under sealed conditions using water proof packaging to avoid a glass transition decrease of the product due to moisture pick up.

Preferably, the solidified glucose obtained according to the inventive method contains at least 50 wt % DS of glucose, more preferably at least 60 wt % DS of glucose and most preferably at least 70 wt % DS of glucose. Preferably, the solidified glucose obtained according to the inventive method contains at most 99 wt % DS of glucose, more preferably at most 95 wt % DS of glucose, even more preferably at most 90 wt % DS of glucose and most preferably at most 80 wt % of glucose. For instance, the glucose in solid form i.e. the solidified glucose obtained according to the inventive method may comprise or (essentially) consist of less than 50 wt % dry DS fructose and at least 50 wt % DS of glucose; for instance, 40 wt % DS fructose and 60 wt % DS glucose; or for instance, 42 wt % DS fructose and 53 wt % DS glucose.

The present invention further relates to food, feed, personal care, nutraceutical, pharmaceutical or industrial product comprising the solidified glucose of the present invention and optionally additional ingredients. The food product may be confectionery product, beverage, bakery, dairy, or frozen products. Solidified glucose may also be used as an excipient in pharmaceutical products such as powdered medicines, tablets and the like and in confectionery tablets.

Methods Of Measurement

Moisture content ("MC"): The moisture content was determined with an infrared moisture balance (MA30, Satorius). The sample was dried at 105° C.

The moisture content (in wt %) was calculated as (A1−A2)/A1×100 where A1 was the weight of the sample before drying in the oven and A2 was the weight of the resulted dried sample.

Dry substance content ("DS") is measured according to formula:

$$DS\ (\%)=100\%-MC\ (\%)$$

Particle size distribution: The particle size distribution was measured by laser diffraction (Beckman Coulter, LS 13 320, Miami, Florida). Samples were poured into a stirred tank, filled with pure ethanol and circulated 2 times into the measuring cell (pumping rate 30%). Laser light having 750 nm wavelength was used as the main laser light source, whereas laser light having wavelength of 450, 600, and 900 nm was used for polarization intensity differential scattering (PIDS). The detection range was 0.04-2000 μm. The volumetric particle size distributions of the samples were calculated from the intensity distributions of the scattered light according to the Fraunhofer optical model using the instrument's software (plant cell wall RI=1.6, water RI=1.33 and absorption coefficient for the dispersion 1) (Verrijssen et al., 2014).

Average particle size may be determined by ASTM C136-06.

Tg: A thermomechanical analysis (TMA) uses a small sample of material, which is heated on a quartz stage. A rod inside the machine places a small amount of force on the top of the sample, and the movement of the rod is measured with a linear variable differential transformer or LVDT. The entire instrument is heated at a slow rate, usually 5° C. per minute. This data is reported as a curve, where change in length is plotted versus temperature. The slope of the resulting curve is called the coefficient of linear thermal expansion, or COLTE. The glass transition temperature is the point at which the slope of the line changes.

Microscopy Analysis: The microstructure of the non-homogenised and homogenised samples was visualised by means of microscopy, using specific dyes and epifluorescent lightening, as well as normal light. The epifluorescent samples were stained with acridine orange (dilution of 1:100 from 2% concentrated dye) and analysed using an Olympus BX-41 microscope, equipped with an Olympus XC-50 digital camera and photo-analysing software. Acridine orange was used as a cationic dye which associates with polyanionic compounds while emitting a green fluorescence.

Flowability measurement method: The angle of repose is the angle (relative to the horizontal base) of the conical pile produced when a granular material is poured on to a horizontal surface. It is mainly related to the density, surface area and coefficient of friction of the material concerned. The angle of repose attachment comprises a 100 mm diameter circular test platform together with a digital height gauge having a range of 0-300 mm For this particular test, the funnel is normally equipped with a special 10 mm i.d. nozzle mounted 75 mm above the test platform. The angle of repose can be determined by reading off the height of the powder cone in mm from the digital display of the height gauge and dividing the reading by 50.

Hydrophilicity measurement method: the degree of hygroscopicity of a substance is defined based on the percentage increase of mass of the substance after 24 hours of exposure at 80±2 per cent relative humidity and 25±1° C. A substance is extremely hygroscopic if the mass increase at the above conditions is equal or higher than 15%.

Measuring Color (CIELAB L*, b* values): CIE L*a*b* (CEILAB) is the most complete color space specified by the International Commission on Illumination (Commission Internationale d'Eclairage). It describes all the colors visible to the human eye and was created to serve as a device independent model to be used as a reference. The L* and b* values are obtained by placing samples (in powder form) in the glass cell (fill the cell to about a half) of the colorimeter and analyse the sample in accordance with the user's instructions of the colorimeter. The colorimeter used is a Minolta CR400 Colorimeter.

The invention will now be described with the help of the following examples and comparative experiments, without being however limited thereto.

EXAMPLES

Example 1

Approximately 500 g of a glucose-fructose syrup having a dry substance (DS) content of 70 wt %, 53 wt % DS of glucose and a 42 wt % DS of fructose were evaporated in a jacketed vessel under vacuum, at an absolute pressure of around 0.05 bar. The syrup was gently stirred by means of a blade propeller. The evaporation took place at 60° C. and the produced steam went into a cylindrical condenser, fitted with a coil internally refrigerated by a thermostatic fluid at −1° C. The condensed water fell down into a cylindrical vessel maintained a few degrees over 0° C. The collected water amount was evaluated by the liquid height in the vessel at the condenser bottom. After a few hours, when the DS percentage was around 94%, 35 g of solid glucose monohydrate having a dry substance content of 92 wt % and a glucose content of 99.5 wt %, in the form of particles having a particle size D50 of 160 μm and a particle size distribution in the range of 1 μm to 1500 μm, were poured into the syrup in order to induce a partial crystallization of the amorphous glucose. 10 minutes later a small amount of the slurry, at semi-crystalline state, was withdrawn from the vessel, quenched over a cylinder internally refrigerated at a temperature around 2° C. Due to the very rapid cooling and quenching, the glucose slurry immediately solidified. The obtained solid product appeared transparent and fragile. The solid was then put in a cylindrical container, at 2° C., where it was ground down to particles between 500 μm and 2-3 mm. Finally, the glucose particles were put over a vibrating surface where they were let to jump together with 35 g of the same solid glucose monohydrate as used for the seeding step for 20 minutes. After the coating process the obtained glucose particles were separated from the coating powder by sieving. During this drying process, the temperature of the particles was naturally increased from a few degrees until the ambient temperature. A partial transformation of the product was observed and it was assumed to be the transformation of amorphous glucose to crystalline glucose. The produced particles, spherical and non-sticky, were saved in a sealed sample holder. After a period of time of 30 days the particles exhibited no agglomeration, very low fragility, and thus their conditions appeared very stable.

Dissolution speed tests of the produced semi-crystalline particles were performed by comparison with the dissolution speed of pure crystalline glucose i.e. glucose monohydrate. Two comparative runs were carried out by using an initial mass of 1.5 g of solid inventive semi-crystalline glucose particles vs. crystalline glucose monohydrate, both having particle sizes in the range of 425-600 μm. The solid was stirred in a cylindrical vessel with distilled water at ambient temperature. In both the runs the solid disappearance was detected after 25 s, showing an equal dissolution speed of the produced semi-crystalline glucose in comparison to the crystalline glucose monohydrate.

Example 2

Approximately 500 g of the same glucose-fructose syrup as used in Example 1 was evaporated as reported in Example 1, until a dry substance of about 94 wt % was reached. Then, 28 g of solid anhydrous glucose having a dry substance content of 99.5 wt % and a glucose content of 99.5 wt %, in the form of particles having a particle size D50 of 210 μm and a particle size distribution in the range of 1 μm to 1500 μm was added as the seeding material and mixed with the syrup for 10 minutes, at which point a homogeneous slurry was obtained. The presence of anhydrous glucose powder induced a partial crystallization of the amorphous glucose. A sample of the slurry was withdrawn and laid over a cooled surface, internally refrigerated at around 2° C. The so-called semi-crystalline solid glucose at glassy state was removed from the cold surface and ground in a refrigerated vessel, down to a size of a few mm Then, the produced solid particles were let to jump with 30 g of the same solid anhydrous glucose as used for the seeding step for 20 minutes. At the end of the overall process the characteristics of the obtained particles resulted quite similar to those produced in Example 1.

Comparative Experiment

For the sake of comparison, according to the conventional prior art method of crystallisation to produce crystalline glucose by starting from a raw material having a 74.5% DS syrup and even with a very high glucose content of 94% DS, only a yield of at most 50% solid glucose can be obtained, as will be demonstrated below.

A syrup with 74.5% DS and a glucose content of 94 wt % DS can be seeded with 10% (based on the dry substance of the syrup) of pure glucose monohydrate powder as used in Example 1 above. The slurry can be heated and maintained under stirring for 10 minutes at constant temperature of 50° C. to suspend and distribute the crystals in the suspension. The slurry within the vessel can then be cooled for a period of 30 hours down to a temperature of 25° C. at a slow, constant cooling rate of 0.8° C. per minute. The slurry can then be centrifuged at 1000g for 15 minutes. The obtained crystals can be rinsed by spraying the crystals with an amount of water representing 5 wt % of the mass of crystals. The crystals can then be dried to a moisture content of 9 wt % and sieved. This would result in a yield of not more than 50% based on the dry substance of glucose available in the starting syrup for crystallisation.

Furthermore, in this case, the mother liquor needs to be recycled i.e. the process has to be repeated to extract and obtain more final product from the mother liquor, requiring high energy consumption and high costs.

On the contrary, the production process of the semi-crystalline glucose according to the invention led directly to the final product and no recycling streams were needed. In the process according to the invention, the production yield was equal to 100% of the solute glucose initially present in the syrup, whereas in the case of the process according to the prior art the yield was less than 50%.

Furthermore, there were differences in the duration of the process. In the process according to the invention, after the first evaporation, the inventive semi-crystalline glucose were obtained in less than 1 h (see Example 1), whereas the production of crystalline glucose according to the prior art would require a much longer time.

Finally, the semi-crystalline glucose produced according to the inventive method can be immediately packaged. However, this is not the case of crystalline glucose produced according to the prior art, which requires further downstream processing before packaging can take place, in particular the separation from the mother liquor, drying, cooling, sieving and packing. During these down processing steps further losses of fine dust could be experienced.

The invention claimed is:

1. A glucose in solid form comprising:
   a matrix phase comprising amorphous glucose and at least 2 wt % water by weight of the matrix phase, and having a glass transition temperature (Tg) higher than 25° C.; and
   a disperse phase comprising a plurality of carbohydrate crystals within said matrix phase,
   wherein the carbohydrate crystals comprise glucose and optionally one or more other carbohydrate(s), wherein the glucose in solid form comprises at least 50wt % by dry substance (DS) of glucose, and optionally wherein the glucose in solid form is coated with a dry powder coating.

2. The glucose in solid form according to claim 1 comprising at least 60wt % DS of glucose.

3. The glucose in solid form according to claim 1, wherein the dry powder coating is selected from sweeteners, starches, polyols, dextrins, and maltodextrins and mixtures thereof.

4. The glucose in solid form according to claim 1, wherein the one or more other carbohydrate(s) comprised in the carbohydrate crystals are selected from sweeteners and/or polyols.

5. The glucose in solid form according to claim 1, wherein the matrix phase containing the amorphous glucose has a glass transition temperature (Tg) of at least 26° C.

6. The glucose in solid form according to claim 1, wherein the dry powder coating has a glass transition temperature (Tg) higher than 25° C.

7. The glucose in solid form according to claim 1, wherein the matrix phase and carbohydrate crystals essentially consist or consist only of glucose and water, and wherein the glucose in solid form is coated with a dry powder coating that is different from glucose or does not essentially consist or consist only of glucose.

8. The glucose in solid form according to claim 1, wherein the matrix phase is in an amount of at least 70% DS; and/or wherein the amorphous glucose is present in an amount of at least 0.1 wt % relative to the total mass of the glucose; and/or wherein the water is present within the matrix phase in an amount of at least 0.2 wt % relative to the total mass of the glucose; and/or wherein the dispersed phase plurality of carbohydrate crystals is present in an amount of at least 20 wt % relative to the total mass of the glucose.

9. The glucose in solid form according to claim 1, wherein the glucose in solid form is in the form of a powder comprising particles having a D50 of at least 10 um.

10. The glucose in solid form according to claim 9, wherein the dry powder coating contains coating particles, said coating particles having a D50 that is at least 15% smaller than the D50 of the particles forming the powder.

11. The glucose in solid form according to claim 1 having one or more of:

a CIELAB L* value of at least 85;

a flowability between 20 and 45 degrees expressed as angle of repose;

a hydrophilicity between 15% and 50% measured after 24 hours of exposure to water at 80% +2% relative humidity and 25 +1° C.

12. A powder containing the glucose in solid form of claim 1.

13. A method of manufacturing solidified glucose comprising:

(i) providing an aqueous glucose solution having a dry substance (DS) of at least 80 wt % relative to the total mass of the solution;

(ii) providing a powder containing particles comprising a carbohydrate material;

(iii) adding the powder to the aqueous glucose solution to obtain an aqueous slurry having a glass transition temperature (Tg) higher than 25° C.;

(iv) cooling the aqueous slurry to a temperature of at most the Tg of said slurry thereby obtaining a product containing solidified glucose comprising an amorphous phase with amorphous glucose and at least 2 wt % water by weight of the matrix phase, and having a glass transition temperature (Tg) higher than 25° C.; and (v) optionally milling the product containing the solidified glucose and/or coating the solidified glucose or the milled solidified glucose.

14. The method according to claim 13 wherein the solidified glucose is a glucose in solid form containing a matrix phase and a plurality of carbohydrate crystals within said matrix phase, the matrix phase containing amorphous glucose and water, wherein the carbohydrate crystals comprise glucose and optionally one or more other carbohydrate(s), wherein the glucose in solid form comprises at least 50wt % by dry substance (DS) of glucose, and optionally wherein the glucose in solid form is coated with a dry powder coating.

15. A food, feed, personal care, nutraceutical or pharmaceutical product comprising the glucose in solid form according to claim 1 and additional ingredients.

16. A food, feed, personal care, nutraceutical or pharmaceutical product comprising the powder according to claim 12 and additional ingredients.

* * * * *